United States Patent [19]

Soini et al.

[11] Patent Number: 4,587,223
[45] Date of Patent: * May 6, 1986

[54] METHOD FOR QUANTITATIVE DETERMINATION OF A BIOSPECIFIC AFFINITY REACTION

[75] Inventors: Erkki Soini; Ilkka Hemmilä; Timo Lövgren, all of Turku, Finland

[73] Assignee: Wallac Oy, Turku, Finland

[ * ] Notice: The portion of the term of this patent subsequent to Feb. 15, 2000 has been disclaimed.

[21] Appl. No.: 526,331

[22] Filed: Aug. 25, 1983

[30] Foreign Application Priority Data

Sep. 13, 1982 [SE] Sweden .................... 8205211

[51] Int. Cl.⁴ .................. G01N 33/536; G01N 21/76; G01N 33/566; G01N 33/533
[52] U.S. Cl. .................. 436/536; 436/172; 436/501; 436/546; 436/800
[58] Field of Search ............... 436/172, 501, 537, 546, 436/800, 536

[56] References Cited

U.S. PATENT DOCUMENTS

| 4,199,559 | 4/1980 | Ullman et al. | 436/537 |
| 4,208,479 | 6/1980 | Zuk et al. | 436/537 |
| 4,220,450 | 9/1980 | Maggio | 436/537 |
| 4,283,382 | 8/1981 | Frank et al. | 436/546 |
| 4,374,120 | 2/1983 | Soini et al. | 436/800 |

FOREIGN PATENT DOCUMENTS 79020798 6/1983 Sweden .

OTHER PUBLICATIONS

Rubinstein et al., Biochem. Biophys. Res. Com. 47, (1972), pp. 846–851.
Leute et al., (1972) JAMA 221, pp. 1231–1234.
Ullman et al., (1976) J. Biol. Chem. 27, pp. 4172–4178.
Kohen et al., (1979) Feb. Letters 104, pp. 201–205.
Smith et al., (1981) Ann. Clin. Biochem. 18, 253–274.
Ullman, (1981), "Recent Advanaces in Fluorescence Immunoassay Techniques".
Crosby et al., (1961) J. Chem. Phys. 34, p. 743.
Crosby et al., (1962) J. Phys. Chem. 66, p. 493.
Filipescu et al., (1964) J. Phys. Chem. 68, p. 324.
Sinha, (1966), Complexes of the Rare Earths, Pergamon Press, New York.

Primary Examiner—Christine M. Nucker
Assistant Examiner—Stephen Wieder
Attorney, Agent, or Firm—Fisher, Christen & Sabol

[57] ABSTRACT

Method for quantitative determination of a biospecific affinity reaction in which an immunochemical compound labelled with a lanthanide chelate is used which can be detected by means of time-resolved fluorescence in which the amount of labelled compound present in the biospecific affinity reaction can be measured without the separation of free and biospecifically bound labelled compound having to be carried out.

2 Claims, 2 Drawing Figures

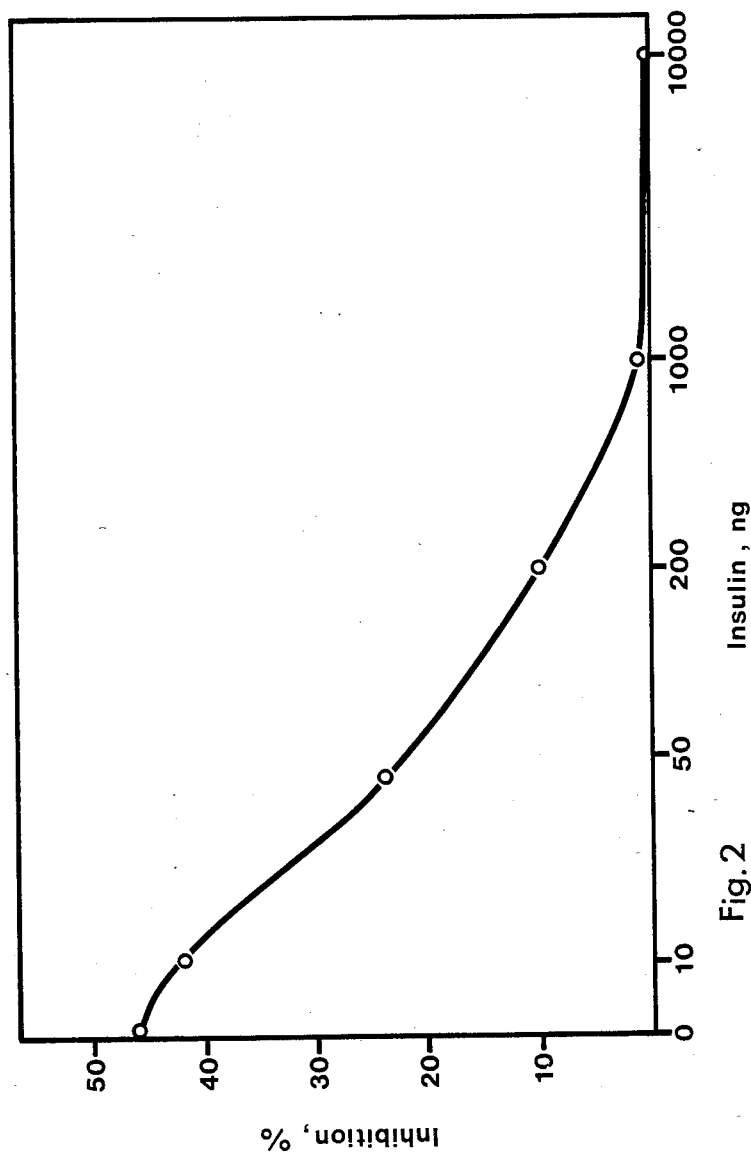

METHOD FOR QUANTITATIVE DETERMINATION OF A BIOSPECIFIC AFFINITY REACTION

BACKGROUND OF THE INVENTION

Prior Art

Immunological methods for quantitative determinations based on the use of non-radioactive markers have been developed during the latest decade. One of the most important improvements within this research was the development of homogeneous immunoanalytical systems, which Rubinstein and his collaborators (see: (1972) Biochem. Biophys. Res. Com. 47, 846–851) defined as determinations which do not require any separation step. As the separation step can be left out, one source of errors is eliminated and at the same time, the execution of the analysis becomes easier, which flavors the automatization of an analysis method.

A homogeneous immunoanalysis thus means a system where both the reaction between antibody and ligand (hapten and antigen) and the determination of the degree of reaction of these are carried out in a homogeneous solution. The separation between "free" and "antibody-bound" compound can be avoided if the properties of the marker are affected by the reaction between antibody and ligand. In principle, two different types of homogeneous immunoassay systems have been developed. The reaction affects the physical properties of the marker or the reaction affects via the marker a biological activity which can be followed. In most homogeneous immunoassay systems a labelled ligand (Lg-M) is used, which reacts with a specific antibody (Ab) and an unknown ligand (Lg) the amount of which is to be determined.

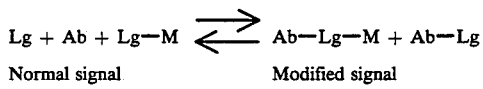

Normal signal     Modified signal

When the antibody binds the labelled ligand the signal used for the analysis will be modified. In such a system the intensity of the measured signal can directly be related to the unknown concentration of the ligand in the sample. Immunochemical markers, which have been used to label ligands and which after the reaction with the antibody due to a changed physical environment give a modified signal, comprise free radicals (see Leute et al. (1972) JAMA 221, 1231–1234), fluorescent molecules (see Ullman et al. (1976) J. Biol. Chem. 27, 4172–4178) and chemiluminescent molecules (see Kohen et al. (1979) Febs Letters 104, 201–205).

A relatively large number of homogeneous fluorescence spectroscopic immunoanalytical methods have been developed, all of which are based on the fact that the biospecific affinity reaction affects in one way or the other the physical properties of the marker so that a change of signal can be registered. This change of signal which is fluorescence spectroscopically registered can for example consist of quenching, change in polarization, excitation transfer or protection. Comprehensive surveys have recently been published which give a good survey of the fluoroimmunoassay determinations known at present which can be carried out in homogeneous systems (see Smith et al. (1981) Ann. Clin. Biochem. 18, 253–274, Ullman (1981) "Recent Advances in Fluorescence Immunoassay Techniques".

In the above mentioned surveys the limitations to which both heterogeneous and homogeneous fluorescence immunoassay determinations are subject are also described, namely the high background fluorescence which follows all conventional fluorescent markers and fluorescence spectroscopic analyses. This has constituted the greatest limitation for a further development of sensitive methods of analysis based on fluorescence.

BROAD DESCRIPTION OF THE INVENTION

The present invention revolves to a method in which the advantages of the time-resolved fluorescence are combined with a homogeneous analysis principle in biospecific affinity reactions, especially immunological reactions.

The invention more specifically a method for the quantitative determination of a biospecific affinity reaction, especially an immunological reaction in solution, in which especially an immunochemical compound labelled with an indicating group is used, the indicating parameter of which is affected when the compound reacts and forms a complex with an immunochemical counterpart which shows specific affinity to the labelled compound, so that it will be possible to determine the amount of labelled compound present in the biospecific affinity reaction or the immunochemical complex, no separation of free and biospecifically bound labelled compound then having to be carried out. In this connection, immunochemical compound refers especially to antigens and haptens and immunoglobulines including for example Fab- or Fc-fragments.

The indicating group consists of a lanthanide chelate which can be indicated by means of a time-resolved fluorescence. The indicating parameter is at least one of the intensity and the half-life.

The formed complex, for example, quenches time-resolved fluorescence by preventing the forming of an energy absorbing ligand field around the labelled group. Examples of the lanthanide are europium and terbium. The ligand field of the lanthanide chelate, for example, can be formed of a $\beta$-diketone, a synergetic compound, for example, trioctylphosphine oxide or a mixture of these.

DETAILED DESCRIPTION OF THE INVENTION

Figure 1:
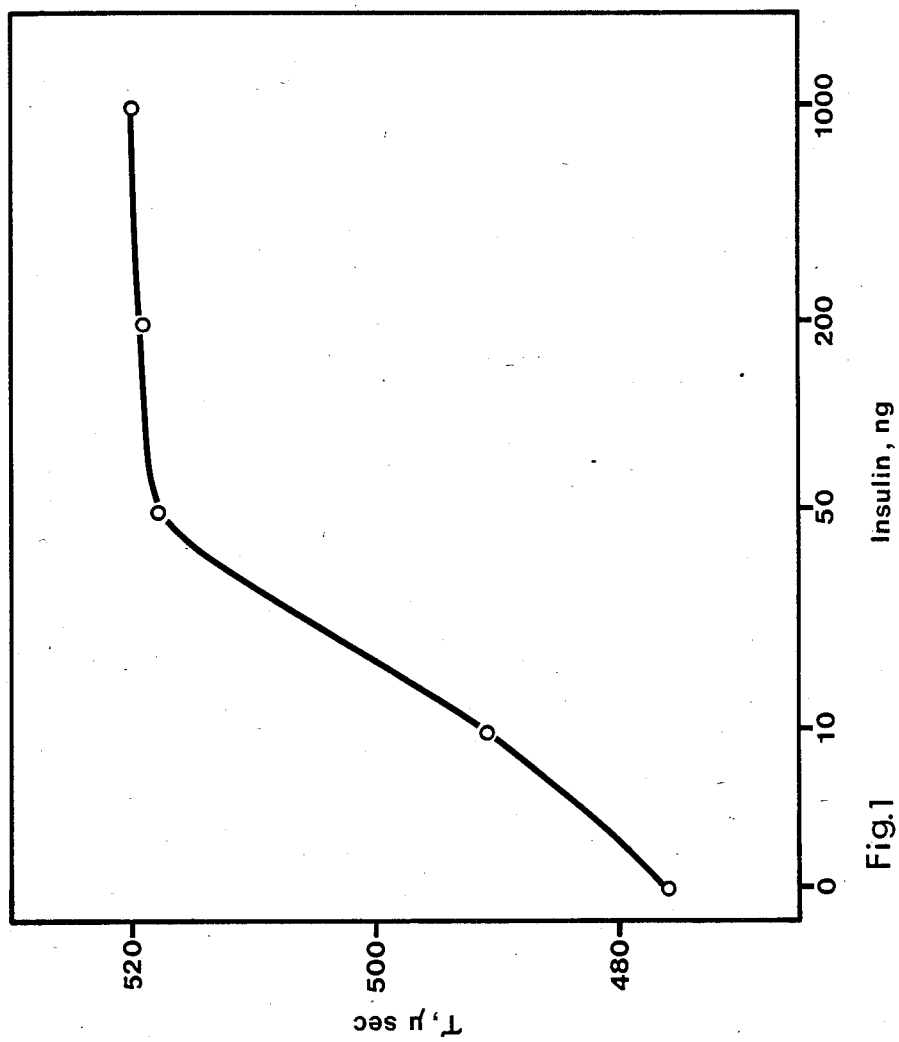

The invention will now be explained in detail, reference being made to two examples of execution, the first one being illustrated by the diagram in FIG. 1 and the other one by the diagram according to FIG. 2.

In time-resolved fluorescence the fluorescent marker is excited by means of a pulsating light impulse of a short duration and the fluorescence is not detected until a certain time has elapsed from the excitation pulse. During the time passing between the excitation and the detection the fluorescence from possible sources of interference will decay, so that only the signal from the marker useable for time-resolved fluorescence is detected. Such a marker ought to have as high fluorescence as possible, a relatively long emission wavelength, a large Stokes shift and a chemical structure which makes it possible to couple the marker covalently to antigens, haptens and antibodies. A fluorescence marker which fulfils the above mentioned requirements is described in Swedish Patent Application No. 7902079-8 and consists of a lanthanide chelate formed of a lanthanide and an aromatic β-diketone, the lanthanide being bound to the antigen, hapten or antibody via an EDTA-analogue, so that a fluorescent lanthanide chelate complex is formed. The fluorescent life time of the marker is long, 50–1000μsec, which makes it extremely suitable for the time-resolved detection principle. The fluorescence from the marker can either be measured when the marker is bound to the antigen, hapten or antibody or the lanthanide can at suitably chosen conditions be released from these, the fluorescence thus being brought about in solution in the presence of an aromatic β-diketone and a synergetic compound as for example trioctylphosphine oxide. The latter method is described in Swedish Patent Application No. 8102753-4.

In time-resolved fluorescence which is based on the fact that lanthanide chelates are used as fluorophores the intensity of the fluorescence and its life time is completely dependent on the properties of the chelate, i.e. the labelled ligand. Lanthanide ions in solution have a very low fluorescence intensity, which in itself is dependent on the electron configuration of the ions. Among the lanthanides europium and terbium have the most favourable configuration. In spite of the fact that the fluorescence originates from the metal ion it has however been found that the organic ligands taking part in the procedure have a very important function (see Crosby et al. (1961) J. Chem. Phys. 34, 743, Crosby et al. (1962), J. Phys. Chem. 66, 493). For example, the lanthanide-β-diketone chelate (M (β-diketone)$_3$) has a very intensive fluorescence, the intensity and life time of which is dependent on the β-diketone present in the chelate and the composition of the surrounding solution (see Filipescu et al. (1964) J. Phys. Chem. 68, 324, Sinha (1966) in Complexes of the Rare Earths, Pergamon Press, New York). To make the lanthanide ion fluorescent when chelated at least the following conditions ought to be fulfilled:

1. The organic ligand ought to be excited. The ligand with suitable electronorbitals ($\pi$) absorbs energy (a photon) and is excited then from a singlet ground state to one of the vibration levels in the first excited singlet state.

2. An energy transition in the ligand ought to take place. The energy is transferred from one excited singlet state to an excited triplet state in the ligand.

3. Conditions for an intramolecular energy transition within the lanthanide chelate ought to exist. The energy is transferred from the excited triplet state of the ligand to the resonance level of the lanthanide ion. To make this happen and to cause an intensive fluorescence characteristic for the lanthanide at least one of the resonance levels of the lanthanide ion ought to be at an energy level which is somewhat below that of the excited ligand. Furthermore, the excited triplet state of the ligand ought to have a relatively long life time.

4. The light emission ought to take place from the lanthanide ion. The metal ion reverts to a lower level of energy, the energy then being emitted in the form of a photon. The emission spectra of the lanthanide chelate is characteristic for the lanthanide ion, but the ligand and the surrounding environment will affect the other physical properties of the fluorescence.

In the earlier described principle for homogeneous immunoassay a biospecific affinity reaction is carried out in solution without a separation between "free" and "antibody-bound" compound, the physical properties of the marker, for example, then being affected by the reaction between antibody and ligand. In the present invention the advantages of time-resolved fluorescence with lanthanide chelates as markers, have been combined with this homogeneous analysis principle. In homogeneous analysis the labelled compound (antigen, hapten or antibody or the reacting compounds in a biospecific affinity reaction) will be bound to biospecific centra in for example the antibody, the chemical environment around the labelled component then being changed. If the marker consists of a lanthanide chelate the binding to the antibody or the biospecific molecule will most likely affect the ligand field around the lanthanide ion by affecting one or some of the factors taking part in the adsorption, transition and emission of the excited energy. The binding of an antigen labelled with a lanthanide chelate to a specific antibody can for example cause the following changes useable for homogeneous analysis in the physical fluorescence signal registered by means of time-resolved fluorescence:

1. A change in the intensity of the time-resolved fluorescence is caused by the fact that the binding to the antibody affects the properties of the ligand field around the lanthanide ion. This means that the signal measured can due to the change mentioned either increase or decrease in intensity.

2. A change in the half-life (decay time) of the time-resolved fluorescence. This change can be coupled to a change of intensity or the half-life can be affected while the quantum yield is unchanged. The half-life can either be prolonged or shortened dependent on the changes in the ligand field.

3. An inhibition of the forming of an energy absorbing ligand field around the lanthanide ion bound to the antigen. If the lanthanide ion is bound to the antigen via a chelate which cannot absorb the excitation energy necessary for the fluorescence, but the homogeneous analysis system requires for example β-diketones to be able to form the ligand field around the lanthanide ion necessary for the energy adsorption, the binding between the antibody and antigen will prevent the forming of this ligand field.

According to the invention the described principles are used in homogeneous biospecific affinity reactions. The invention will be further explained below by means of a number of non-limiting examples of execution.

EXAMPLE 1

A homogeneous immunological determination of insulin with time-resolved fluorescence by measuring changes in the half-life (decay time).

Europium labelled insulin was produced by conjugating aminophenyl-EDTA-Eu to insulin, the Eu-chelate first being changed to an isothiocyanate derivative which is used for the conjugation. 1.4 mg of insulin was dissolved in 0.5 ml 0.1M borate buffer, pH 9.3 and thereafter twice the equivalent amount of isothiocyanate derivative of aminophenyl-EDTA-Eu was added. The reaction took place over night at room temperature. The free marker was separated from labelled insulin by gel filtration (Sephadex G-25). The degree of conjugation was determined to 0.5 Eu/insulin molecule by comparing the fluorescence intensity of the conjugate with an Eu-solution of a known concentration.

The immunoassay was carried out in polystyrene tubes (12×55 mm) to which 10 μl anti-insulin serum (diluted 1→20) was pipetted, 10 μl labelled insulin (20 ng), 70 μl 0.05M Tris-HCl buffer, pH 7.7 containing 0.5% BSA, 0.05% bovine IgG and 50 μM DTPA, 10 μl insulin standard (0, 10, 50, 200, 1000 and 10 000 ng), and 1.0 ml of a solution containing 20 μM β-NTA, 100 μM TOPO, 0.3% Tween 20, 0.15M NaCl in 0.05M Tris-HCl buffer pH 8.0. The samples were incubated for 4 hours at 37° C. whereafter the fluorescence for each sample was measured in 10 μsec at different times after the excitation (100, 200, 300, 400, 480 and 600 μsec). Every sample was measured ten times. The result appears in Table 1.

TABLE 1

The fluorescence intensity of insulin standards measured at different times after the excitation.

| Time after excitation | Insulin concentration (ng) | | | | | |
|---|---|---|---|---|---|---|
| | 0 | 10 | 50 | 200 | 1000 | 10000 |
| 100 | 11374 | 13364 | 17850 | 19385 | 22122 | 26172 |
| | ±112 | ±123 | ±132 | ±150 | ±157 | ±240 |
| 200 | 9850 | 11578 | 15602 | 17010 | 19613 | 22892 |
| | ±96 | ±96 | ±102 | ±136 | ±88 | ±144 |
| 300 | 8441 | 10225 | 13630 | 14871 | 16746 | 19846 |
| | ±130 | ±137 | ±146 | ±176 | ±238 | ±152 |
| 400 | 7518 | 8825 | 12013 | 12702 | 14819 | 17557 |
| | ±120 | ±119 | ±96 | ±120 | ±179 | ±241 |
| 480 | 7039 | 8376 | 11078 | 12042 | 13940 | 16330 |
| | ±123 | ±145 | ±112 | ±128 | ±83 | ±211 |
| 600 | 5847 | 6914 | 9030 | 9768 | 11458 | 13888 |
| | ±104 | ±174 | ±264 | ±134 | ±110 | ±88 |

As the change of the intensity of the signal follows the kinetics of a first order reaction the half-life of the fluorescence intensity for the insulin concentrations used was determined. The intensity of the fluorescence decreased faster at a low amount of insulin than at a high amount. The calculated half-lives were used for the drawing of a standard curve according to FIG. 1 in which the coordinate indicates the half-life in microseconds and the abscissa the amount of insulin in nanograms.

EXAMPLE 2

A homogeneous immunological determination of insulin by measuring the inhibition of the forming of an energy absorbing ligand field around the labelled insulin which has bound antibody.

Europium labelled insulin was produced according to the method described in FIG. 1. The immunoassay determination was carried out in polystyrene tubes (12×55 mm) to which 70 μl 0.05M Tris-HCl buffer pH 7.7 was pipetted containing 0.5% BSA and 50 μM DTPA, 10 μl anti-insulin serum (diluted 1→20), 10 μl insulin (20 ng), 10 μl insulin standard (0, 10, 50, 200, 1000, 10 000 ng) and 1.0 ml of a solution containing 20 μM β-NTA, 100 μM TOPO, 0.3% Tween 20, 0.15M NaCl in 0.05M Tris-HCl buffer pH 8.0. The tubes were incubated for four hours at 37° C. whereafter time-resolved fluorescence for each sample was measured in 250 μsec, 50 μsec after the excitation. According to the determination principle the fluorescence intensity of the sample decreases, as the amount of "cold" insulin increases. The result appears from FIG. 2, where in the coordinate the inhibition is indicated in per cent and in the abscissa the amount of insulin in nanogram.

We claim:

1. Method for quantitative determination of a homogeneous immunological reaction, comprising reacting a labelled immunochemical compound with its immunochemical counterpart, labelling the immunochemical compound with a europium or terbium chelate, wherein the improvement comprises measuring the intensity and/or the half-life of the fluorescence of the chelate by excitation of the chelate with a light pulse, and detection of the fluorescence after a predetermined time has elapsed from that light pulse.

2. Method according to claim 1, wherein the chelate contains a β-diketone and/or trioctylphosphine oxide.

* * * * *